United States Patent [19]
Yamamoto

[11] Patent Number: 4,930,851
[45] Date of Patent: Jun. 5, 1990

[54] IMAGE MAGNIFYING AND PICK-UP SYSTEM WITH LIGHTING LIGHT-GUIDE DEVICE

[75] Inventor: Masao Yamamoto, Tokyo, Japan

[73] Assignees: Mitsubishi Kasei Corporation, Tokyo; Scalar Corporation, Tama, both of Japan

[21] Appl. No.: 362,658

[22] Filed: Jun. 7, 1989

[30] Foreign Application Priority Data

Jun. 7, 1988 [JP] Japan ................................. 63-139905

[51] Int. Cl.$^5$ .............................................. G02B 6/14
[52] U.S. Cl. .............................. 350/96.10; 350/96.25; 350/96.26
[58] Field of Search ............... 350/96.10, 96.12, 96.13, 350/96.24, 96.25, 96.26, 96.29

[56] References Cited

U.S. PATENT DOCUMENTS 3,920,980 11/1975 Nath ............................ 350/96.10 X
4,181,398 1/1980 Sick .................................. 350/96.10
4,259,609 3/1981 Month et al. ................ 350/96.10 X
4,676,593 6/1987 Adachi et al. ............... 350/96.10 X
4,740,047 4/1988 Abe et al. ..................... 350/96.10 X

FOREIGN PATENT DOCUMENTS 61-39019 of 0000 Japan .
62-111581 of 0000 Japan .
62-164438 of 0000 Japan .
60-198129 of 0000 Japan .

Primary Examiner—Frank Gonzalez
Assistant Examiner—Phan T. Heartney
Attorney, Agent, or Firm—Oblon, Spivak, McClelland, Maier & Neustadt

[57] ABSTRACT

An image magnifying and pick-up system including a lighting light-guide device for guiding illuminating light to the surface of an observed portion of a specimen. The device includes a light-guide cap mounted at the front end of a lens tube. The light-guide cap includes an outer surface adapted to be abutted against the surface of the specimen, so that illuminating light from optical fibers is guided through the lens tube and light-guide cap may be projected on to the surface of the specimen. The light-guide cap is formed of a transparent material into a substantially hemi-spherical shape and has a central observation aperture, so that the illuminating light may be introduced via an annular end surface of the light-guide cap through the cap to the peripheral surface of the observation aperture.

8 Claims, 3 Drawing Sheets

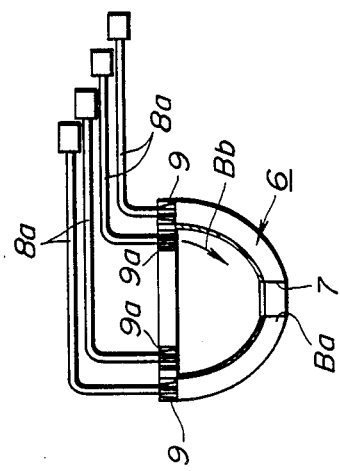
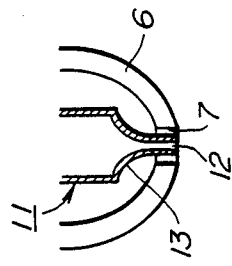
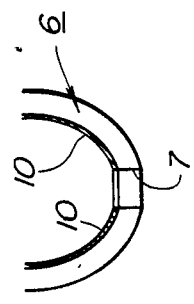
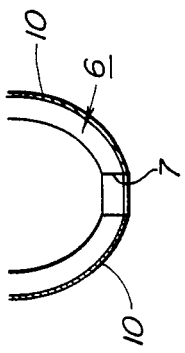
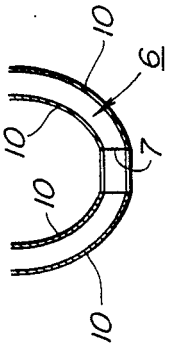
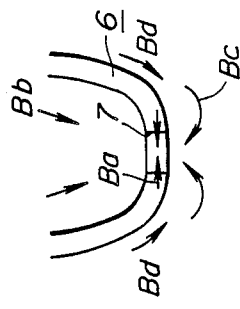

IMAGE MAGNIFYING AND PICK-UP SYSTEM WITH LIGHTING LIGHT-GUIDE DEVICE

BACKGROUND OF THE INVENTION

1. Field of the Invention

This invention relates to an image magnifying and pick-up system incorporating a lighting system directing light on to a portion of any specimen to be observed such as, for example, the skin of a human body, its viscera or the like. Such a magnifying and pick-up system may employ an image Pick-up head section directly abutting the specimen to display a magnified image of the observed portion on a screen of a monitor.

2. Description of the Prior Art

In general, in an image magnifying and pick-up system where the outer surface of an image pick-up head directly abuts a surface of a portion of the specimen to be observed (hereinafter referred to as the "observed portion") to display a magnified image of the observed portion on a monitor screen, it is necessary to illuminate the observed portion.

When the illumination is achieved mainly by using vertical lights or by projecting illuminating light on to the surface of the observed portion (or an abutment surface of the observed portion which the pick-up head abuts in such a way that it is perpendicular to or right opposite the abutment surface), the abutment surface of the observed portion tends to reflect relatively the illuminating light. This causes an observed portion which reflects the light relatively highly to appear very white when projected on to the screen of a monitor, resulting in an unsatisfactory visual impression of the colors and fine detail of the observed portion.

When the illumination is achieved mainly by using horizontal light or by directing illuminating light in parallel to the abutment surface of the observed portion, it is not possible to provide sufficient illumination to any fine recesses in the abutment surface. This therefore causes the recess to be displayed relatively darkly on the screen of the monitor, making effective and accurate inspection of the observed portion impossible.

In order to solve these problems, the present applicants recognized the need for an illuminating or lighting means able to project illumination mainly consisting of horizontal light, but to which vertical light is added in an amount appropriately balanced with the horizontal light onto the surface of the observed portion of the specimen. It was also noted that when the specimen to be observed has a property of transmitting the illuminating light to a certain degree (e.g. human skin or its viscera), the lighting means should also allow adjustment of the balance between vertical light and horizontal light, taking the amount of light transmitted through the specimen into consideration.

Conventional lighting light-guide devices in image magnifying and pick-up systems provide illumination mainly using horizontal light as described above; they therefore fail to meet the requirements outlined above. A lighting lightguide device was therefore proposed which generally includes a transparent cylindrical light-guide body, and a flat disc formed of a transparent light-guide material, mounted at the distal end of the light-guide body through a reflecting surface surrounding the body. It has a central observation aperture in the form of a small hole, so that illuminating light guided through the cylindrical light-guide body to its distal end is refracted on the reflecting surface so as to be directed towards the central axis of the disc. It therefore radiates in the form of horizontal beams from the overall peripheral surface of the observation aperture to illuminate the observed portion of a specimen in the observation aperture.

Unfortunately, this construction necessarily results in only horizontal light constituting the illumination and fails completely to use vertical light and so transmitted light in amounts balanced with the horizontal light.

Also, in this light-guide device, the outer surface of the image pick-up head which abuts the observed portion of the specimen is flat, since it takes the form of a flat light-guide disc. Accordingly, the abutment surface of the observed portion of the specImen is limited to a configuration which is compatible with the outer surface of the head, i.e. a generally convex or flat shape. This causes applications of the light-guide device to be limited.

SUMMARY OF THE INVENTION

Accordingly, it is an object of the present invention to provide a lighting light-guide device for an image magnifying and pick-up system which is capable of efficiently and effectively directing illuminating light to the surface of the observed portion of a specimen.

It is a further object of the present invention to provide such a lighting light-guide device which can afford sufficient illumination to provide a satisfactory magnified display of the observed portion of the specimen, irrespective of any fine recessed configuration that may be present in the observed portion.

In accordance with the present invention, there is provided an image magnifying and pick-up system incorporating a lighting light-guide device comprising: a lens tube; a magnifying optical system located within the lens tube; an image pick-up element at the proximal or rear end of the lens tube for converting an optical image obtained through the optical system into an electrical signal; a light-guide cap mounted at the distal or front end of the lens tube, which is formed of a transparent material and a substantially hemi-spherical in shape, and an illumination system for introducing illuminating light into the light-guide cap from the annular end surface thereof.

In a preferred embodiment of the present invention, the optical fibers each have a distal radiant end surface and are held by an annular retaining ring. The radiant end surfaces of the optical fibers are preferably annularly embedded in the retaining ring while being maintained in close contact with one another, and the retaining ring either contacts with the annular end surface of the light-guide cap or faces the annular end surface of the light-guide cap having a small gap therebetween.

In a Preferred embodiment of the present invention, the light-guide cap is formed into a relatively flat shape at the bottom and the observation aperture is formed at a central portion of the bottom. The cap of a hemi-spherical shape may have a section with a substantially parabolic shape including the relatively flat bottom.

In a preferred embodiment of the present invention, the light-guide cap may have on at least one of its inner and outer surfaces, except for the observation aperture and the annular end surface, a layer with a low refraction index. The layer may be a coating layer or a metal layer applied by vapour deposition.

The system may further comprise a hollow reflection member including a hollow portion and a reflection surface of a parabolic shape formed at a lower section of the hollow portion. The hollow portion is preferably provided with an aperture which is open at the distal end and the distal portion of the hollow reflection member is preferably located adjacent to the inside of the observation aperture of the light-guide cap, in such a manner that the aperture of the hollow portion faces the abutment portion of the specimen which is placed against the light-guide cap.

In a preferred embodiment of the present invention, the optical fibers are distributed to an inner and an outer annular configuration and the optical fibers of each annular configuration are closely contacted to one another and embedded at their distal ends in inner and outer retaining rings, respectively. The outer retaining ring is pressed into contact with the annular end surface of the light-guide cap and the inner retaining ring is positioned inside the outer retaining ring.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which like reference numerals designate like or corresponding parts throughout, wherein:

FIGS. 4 to 6 are schematic sectional views showing modified light-guide caps; and FIG. 7 is a schematic sectional view showing another manner of guiding illuminating light to a light-guide cap.

DETAILED DESCRIPTION OF THE PREFERRED EMBODIMENT

Now, an image magnifying and pick-up system with lighting light-guide device of the present invention will be described with reference to FIGS. 1 to 3.

Figure 1:
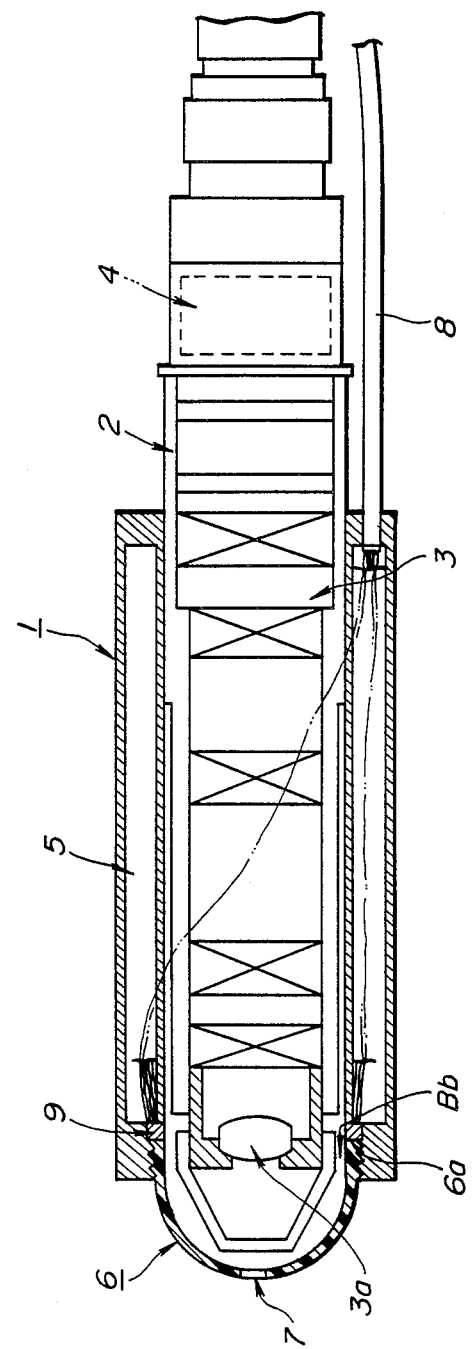
FIG. 1 is a side elevation view partly in section schematically showing an embodiment of a lighting light-guide device for an image magnifying and pick-up system according to the present invention.
Figure 2:
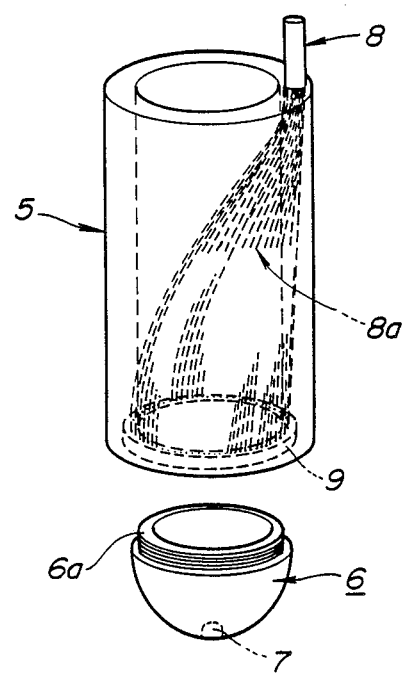
FIG. 2 is an exploded perspective view showing part of the lighting device shown in FIG. 1.
Figure 3:
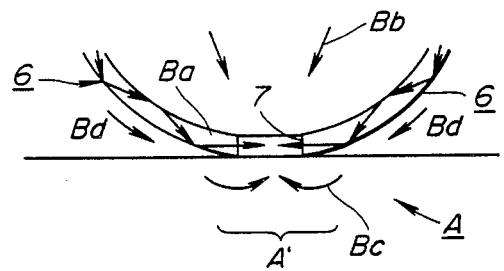
FIG. 3 is a fragmentary enlarged schematic view showing a portion of a light-guide cap of the device of FIG. 1. abutting a specimen.

FIGS. 1 to 3 show a lighting light-guide device which includes a light-guide body 1 substantially constituted by a lens tube 2, a magnIfying optical system 3 within the lens tube 2 and an image pick-up element (CCD image sensor) 4 at the proximal or rear end of the lens tube 2 for converting the optical image obtained through the optical system 3 into an electrical signal. An output corresponding to the image picked up by the pick-up element 4 is supplied to a TV monitor (not shown) connected to the pick-up element 4, so that a magnified image of an observed portion of a specimen against which the device is placed may be visually displayed on the monitor screen.

The device also includes a hollow cylinder 5 closely fitting about the outer periphery of the lower part of the lens tube 2 so as to form a part of the lens tube 2 and a light-guide cap 6 connected on to the distal or front end of the hollow cylinder 5. The cap 6 is opposite an objective lens 3a forming part of the optical system 3 in the lens tube 2. In the illustrated embodiment, the light-guide cap 6 is formed of a transparent synthetic resin material, which permits light to be guided or transmitted within the wall of the cap 6. It has a hemi-spherical shape and is formed with an outer threaded portion through which the cap 6 is detachably fitted to the front end of the cylinder 5 The cap 6 has an annular end surface 6a and at the center of the curved portion, an observation aperture 7 in the form of a small hole.

In use, the light-guide cap 6 is applied to a specimen in such a manner that the outer surface of the cap 6, including the observation aperture 7, is abutted directly against the surface of a specimen at the portion to be observed. For this purpose, the objective lens 3a is positioned so as to focus on the outer surface of the observation aperture 7. Alternatively, the cap may be positioned with its outer surface spaced from the observed surface of the specimen. In this instance, the magnifying optical system 3 may be provided with any focus adjusting means in order to adjust the focus depth of the objective lens 3a.

The device also includes an optical fiber cable 8 comprising a predetermined number of bundled optical fibers 8a introduced through the rear end surface of the hollow cylinder 5. The cable 8 is then separated into the individual optical fibers 8a in the hollow cylinder 5 and these are dispersed in the hollow tube 5, so their front ends are arranged into an annular shape which is substantially continuous or closed. The ends of the optical fibers 8a thus arranged are then fixedly embedded in a retaining ring 9, which is positioned so as to either contact with the annular end surface 6a of the light-guide cap 6 or face the annular end surface 6a of the light-guide cap 6 having a small gap therebetween, thereby forming an optical connection. The other end of the optical fiber cable 8 is connected to a light source (not shown), so that illuminating light emitted from the light source may be introduced via each of the optical fibers 8a, through the end surface 6a of the light-guide cap 6, into the cap 6.

A portion of the illuminating light beams thus introduced from the end surface 6a into the light-guide cap 6 leaks outwardly from the light-guide cap 6 to illuminate the specimen to be observed as light beam Bd, and the remaining portion of the illuminating light beam is repeatedly subject to reflection between the inner surface of the cap 6 and its outer surface (as in the optical fibers 8a), resulting in their being finally collected at the observation aperture 7 at the central portion of the cap 6. Then, the collected light beams are discharged or radiated in the form of horizontal light Ba or in parallel to one another and the surface of the observed portion of the specimen from the peripheral surface defining the observation aperture 7. In addition, a portion of the illuminating light leaks inwardly from the abutment between the annular end surface 6a of the cap 6 and the optical fibers 8a held on the retaining ring 9 and/or any possible cutout portion or the light-guide cap 6 itself. This is scattered in the inside of the light-guide cap 6 to form vertical light beams Bb.

The light-guide cap 6 may have any desired cross-sectional shape as long as light introduced into the cap 6 through the annular end surface 6a may be collected at the observation aperture 7 while repeating reflection in the wall of the cap 6. For this purpose, the cap is desirably formed so as to have substantially hemi-spherically shaped inner and outer surfaces as described above, and to have a relatively small thickness. However, as shown in FIG. 4, the cap 6 maY be substantially hemi-spherical but with a section which is substantially parabolic and which has a somewhat flat bottom surface.

Also, the light-guide cap 6 may have a layer 10 deposited on at least one of its substantially hemi-spherical outer and inner surfaces to promote the reflection of the light within the light-guide cap 6 (though not on the observation aperture 7 and end surface 6a) as shown in FIGS. 5(a), 5(b) or 5(c). The layer 10 may comprise a coating layer with a low refraction index. Alternatively, it may comprise a metal layer formed by vapor deposition. In FIG. 5(a), the layer 10 is applied onto only the inner surface of the light-guide cap 6, and in FIG. 5(b), it is formed on only the outer surface. In FIG. 5(c), it is formed on both inner and outer surfaces.

The vertical light beams or vertically projected light Bb generated along with the horizontal light Ba discharged from the inner peripheral surface of the observation aperture 7 serve as illumination light and may be effectively employed as shown in FIG. 6. Here, a hollow reflection member 11 is used which comprises a body with an elongate hollow portion 12 of a smaller diameter extending outwardly. The member 11 has a reflection surface 13 of a substantially parabolic shape in section formed between the body and the hollow portion 12. The front end of the hollow portion 12 is provided with an aperture. The distal portion of the hollow reflection member 11 is located within the observation aperture 7 of the light-guide cap 6 in such a manner that the aperture of the hollow portion 12 faces the abutment portion of the light-guide cap 6 which abuts the observed portion of the specimen. This construction causes the vertical light Bb scattered in the light-guide cap 6 to be reflected on to the reflection surface 13, and so guided to the observation aperture 7 for illumination.

In order to produce the vertical light Bb more effectively, the construction as shown in FIG. 7 may be employed. Here, the optical fibers 8a are distributed between two inner and outer annular configurations with the optical fibers of each annular configuration being held closely in contact. The optical fibers 8a, thus divided in two, have their ends embedded in two inner and outer retaining rings 9 and 9a, which may be concentric and either contact with or spaced from one another. Then, the outer retaining ring 9 is directed to face the annular end surface 6a of the light-guide cap 6 as in FIG. 1, while the inner retaining ring 9a is positioned inside the outer retaining ring 9. The outer annular ring 9 serves to introduce light into the wall of the light-guide cap 6 in order to produce horizontal light Ba in the observation aperture 7 and the inner annular ring 9a acts to form vertical light Bb in the light-guide cap 6.

The manner of operation of the lighting light-guide device of the illustrated embodiment will be described.

As shown in FIG. 3, the outer surface of the light-guide cap 6 including the observation aperture 7 mounted at the front end of the lens tube 2 of the light-guide body 1 abuts against the surface A' of the observed portion of a specimen A. Illuminating light emitted from the light source is introduced from the optical fibers 8a through the annular end surface 6a into the light-guide cap 6 and a portion of the beams is repeatedly subjected to reflection between the outer surface of the cap 6 and its inner surface, resulting in their being finally collected at the observation aperture 7. Subsequently, the collected light beams are radiated in the form of horizontal light Ba from the inner peripheral surface of the observation aperture.

At the same time, a portion of the illuminating light Bd leaking from the outer surface of the cap 6 and the light Bb leaking from the abutment between the annular end surface 6a of the cap 6 and the optical fibers 8a held on the retaining ring 9, or any possible cutouts or the cap itself in the inside of the cap 6, is radiated in the form of vertical light. This results in the abutment surface A' of the specimen A being illuminated as desired In this instance, when the specimen is light-permeable, light introduced to the specimen A illuminates the abutment surface A' from the inside of the specimen A, and the respective proportions of the illuminating lights may be suitably balanced.

When the abutment surface A' of the specimen A is thus appropriately illuminated, a distinct enlarged or magnified image of the abutment surface A' is formed on the light receiving surface of the image pick-up element 4 through the magnifying optical system 3. The magnified image so-formed may be displayed on the screen of the TV monitor connected to the image pick-up element 4.

In the illustrated embodiment, the light-guide cap 6 is formed into a substantially hemi-spherical shape, accordingly, it is possible to eliminate any possibility that abutment of the light-guide cap 6 against the observed portion A' of the specimen A cannot be satisfactorily achieved due to the configuration of the portion A'. Also, such construction permits any possible fine recesses on the observed portion A' to be distinctly illuminated.

While a preferred embodiment of the invention has been described with a certain degree of particularity with reference to the drawings, obvious modifications and variations are possible in light of the above teachings. It is therefore to be understood that within the scope of the appended claims, the invention may be practiced otherwise than as specifically described.

What is claimed as new and desired to be secured by letters patent of the U.S. is:

1. An image magnifying and picking-up system incorporating a lighting light-guide device system comprising:
   a lens tube;
   a magnifying optical system located within said lens tube;
   an image pick-up element at the proximal or rear end of said lens tube for converting an optical image obtained through said optical system into an electrical signal;
   a light-guide cap mounted at the distal or front end of said lens tube, said light-guide cap being formed of a transparent material and having a substantially hemispherical shape, said light-guide cap comprising an observation aperture at the central portion thereof; and
   an illuminating system for introducing illumination light into said light guide cap from the annular end surface of said light-guide cap thereof;
   whereby a subject at the observation aperture is illuminated by both light guided within said lightguide cap and light having leaked from said light-guide cap.

2. A system as defined in claim 1, wherein said illuminating system includes a light source and optical fibers, the end surfaces of said optical fibers being embedded in an annular retaining ring in close contact with one another and said retaining ring being disposed on said annular end surface of said light-guide cap.

3. A system as defined in claim 1, wherein the inner and/or outer surface of said light-guide cap, excluding said observation aperture and said annular end surface is provided with a layer of material having a low refraction index.

4. A system as defined in claim 3, wherein said material of low refraction index is a coating or a metal layer applied by vapor deposition.

5. A system as defined in claim 1, further comprising a hollow reflection member including a hollow portion with a reflection surface of a substantially concave shape formed at a lower section of the hollow portion, said hollow portion having an aperture at its distal end, said reflection member being located within said observation aperture in such a manner that said aperture in said hollow portion faces the abutment portion of the specimen which is placed against the light-guide cap.

6. A system as defined in claim 2, wherein said optical fibers are distributed to form inner and outer annular configurations; the ends of optical fibers of each annular configuration being closely contacted to one another and embedded in an inner and an outer retaining ring respectively; said outer retaining ring being disposed on said annular end surface of said light-guide cap and said inner retaining ring being positioned inside said outer retaining ring.

7. A system as defined in claim 1, wherein said light-guide cap has a relatively flattened base and said observation aperture is formed at the center of the base.

8. A system as defined in claim 7 wherein said relatively flattened base forms part of a substantially parabolic shape.

* * * * *